United States Patent [19]
Baker et al.

[11] Patent Number: 5,511,159
[45] Date of Patent: Apr. 23, 1996

[54] METHOD OF IDENTIFYING PARAMETERIZED MATCHES IN A STRING

[75] Inventors: Brenda S. Baker, Berkeley Heights, N.J.; Raffaele Giancarlo, New York, N.Y.

[73] Assignee: AT&T Corp., Murray Hill, N.J.

[21] Appl. No.: 242,385

[22] Filed: May 13, 1994

Related U.S. Application Data

[63] Continuation-in-part of Ser. No. 61,782, May 14, 1993, which is a continuation-in-part of Ser. No. 853,459, Mar. 18, 1992.

[51] Int. Cl.$^6$ .................................................. G06F 3/00
[52] U.S. Cl. ................. 395/161; 364/419.14; 364/419.19
[58] Field of Search ..................................... 395/161, 600; 364/419.07, 419.13, 419.14, 419.19

[56] References Cited

U.S. PATENT DOCUMENTS

| | | | |
|---|---|---|---|
| 4,887,212 | 12/1989 | Zamora et al. | 364/419 |
| 4,916,655 | 4/1990 | Ohsone et al. | 395/600 |
| 5,337,233 | 8/1994 | Hofert et al. | 364/419.14 |
| 5,377,349 | 12/1994 | Motomura | 395/600 |
| 5,448,733 | 9/1995 | Satoh et al. | 395/600 |

OTHER PUBLICATIONS

E. M. McCreight, "A Space–Economical Suffix Tree Construction Algorithm," *Journal of the Association for Computing Machinery*, vol. 22, No. 2, 262–272 (Apr. 1976).

D. E. Knuth et al., "Fast Pattern Matching in Strings," *SIAM J. Comput.*, vol. 6, No. 2, 323–350 (Jun. 1977).

R. S. Boyer, "A Fast String Searching Algorithm," *Communications of the ACM*, vol. 20, No. 10, 762–772 (Oct. 1977).

M. Crochemore et al., "Speeding Up Two String–Matching Algorithms," *9th Annual Symposium on Theoretical Aspects of Computer Science*, Cachan, France, 589–600 (Feb. 1992).

R. Giancarlo, "The Suffix of a Square Matrix, with Applications", Proceedings of the Fourth Annual ACM–SIAM Symposium on Discrete Algorithms, Austin, Texas, 1993.

*Primary Examiner*—Raymond J. Bayerl
*Assistant Examiner*—Ba Huynh
*Attorney, Agent, or Firm*—Michele L. Conover

[57] ABSTRACT

Methods are disclosed for finding maximal matches in data strings and for finding matches in parameterized strings, that is, strings containing symbols from more than one alphabet in which the symbols from one of the alphabets are treated as parameters. In general, such maximal matches are found by creating a suffix tree representing the data string, generating lists for each node in the tree indicating the left contexts of all suffixes associated with that node and reporting matches for pairs of suffixes having different left contexts. One method of finding parameterized matches is to substitute a common symbol for the symbols of the alphabet representing the parameters before creating the suffix tree and then discarding matches found for which the actual parameters are not consistent. Another, preferred, method of finding parameterized matches is to substitute integers for the symbols of the alphabet representing the parameters, such symbols being chosen to create a linked list in the data string for each different symbol in such alphabet. Matches found by the suffix tree are then consistent and no matches need be discarded. Other methods of finding matches are disclosed in which suffix trees are used in conjunction with square matrices to analyze the data strings.

6 Claims, 8 Drawing Sheets

FIG. 10B
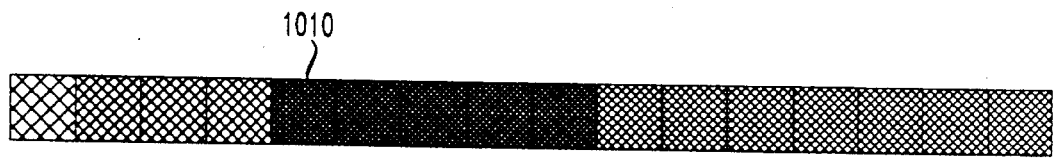
FIG. 10C
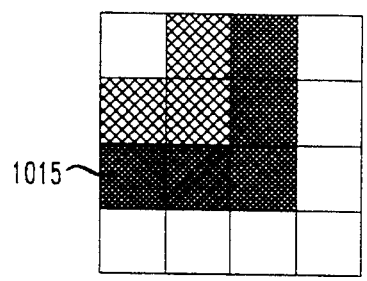
FIG. 10D
FIG. 11A
|   | 1 | 2 | 3 | 4 | 5 |
|---|---|---|---|---|---|
| 1 | a | b | b | a | $ |
| 2 | b | a | b | a | $ |
| 3 | a | b | a | b | $ |
| 4 | a | b | c | a | $ |
| 5 | $ | $ | $ | $ | $ |
FIG. 11B
| 1,1 | 2,1 | 1,2 | 2,2 | 3,1 | 3,2 | 1,3 | 2,3 | 3,3 | 4,1 | 4,2 | 4,3 | 1,4 | 2,4 | 3,4 | 4,4 |
|---|---|---|---|---|---|---|---|---|---|---|---|---|---|---|---|
| a | b | b | a | a | b | b | b | a | a | b | c | a | a | b | a |

PTURBO

PJUMP

METHOD OF IDENTIFYING PARAMETERIZED MATCHES IN A STRING

This is a continuation-in-part of U.S. patent application Ser. No. 08/061,782, entitled "Method of Identifying Pattern Matches in Parameterized Strings and Square Matrices", filed May 14, 1993, currently pending, which is a continuation-in-part of U.S. patent application Ser. No. 07/853,459, entitled "Method and Apparatus for Studying Very Large Sets of Data", filed Mar. 18, 1992, also currently pending.

BACKGROUND OF THE INVENTION

The present invention relates to a method of identifying matches in data strings and square matrices and, more particularly, to a method of identifying non-exact matches in data strings and square matrices.

It is well known that maintenance of large computer programs is a problem because programmers having different programming styles tend to work on the same program. Many times when programmers revise large sections of the program for the purpose of adding new features or revising old features, there is a tendency to duplicate sections of the program and revise the duplicated sections. Such duplication occurs even though it is known that duplicating sections of the program typically makes the program larger, more complex and more difficult to maintain. The programmer usually modifies the duplicated section while still maintaining the old section in the program. The duplicated section may be further copied and modified as the program is revised. In time, the amount of duplication in the program can become substantial, thereby resulting in significant inconsistencies between different sections of the program.

Many times, the ongoing revisions of a program result in sections of the program that are not identical, but are similar in content except for a systematic change in parameter names such as identifiers and constants. For example, in one section of the code the parameters first, last, 0 and fin may be used and in another section of the code these parameters may be replaced by init, final, 1 and g. Identifying these types of approximate matches is difficult since there is no way to identify whether symbols are different because of renaming or because the symbols represent different values.

One way to identify similar code segments is to identify a pattern comprised of parameter names and constant names which represent a particular code segment to be identified. The pattern is compared to a program to identify code segments which match the pattern. However, such a method does not address the situation in which two code segments which perform the same function include parameters which have different names.

A method for identifying exact matches is the Boyer-Moore (BM) method which calculates the number of positions a text string can be shifted, using a text pointer, to avoid a known mismatch based on information contained in two tables as described in R. S. Boyer et al., "A Fast String Searching Algorithm", Commun. ACM, Vol. 20, No. 10, Oct. 1977, pp. 762–772 and D. Knuth et al., "Fast Pattern Matching in Strings," *SIAM J. Comput.*, 6 (1977), pp. 323–350. The first table indicates the smallest number of positions the text pointer can be shifted which will cause a mismatched text symbol in the current alignment to be aligned with a like symbol in the pattern string. The second table indicates the smallest number of positions the text pointer can be shifted which will cause text symbols which match a particular portion of the pattern string to match a different analogous portion of the pattern string after the pattern string has been shifted by a predetermined number of positions. The BM method examines the text symbols in a right to left direction. While this method can detect exact matches, this method is unable to detect nonexact matches.

Similar problems exist for identifying non-exact matches in two dimensional cases, such as square matrices. The ability to identify two dimensional matches is useful in low-level image processing and in conjunction with visual databases which are used in multimedia systems. However, because of the amount of data which must be stored to identify matches, in a square matrix and the time involved in making the necessary comparisons, such matching is normally inefficient and difficult to perform.

SUMMARY OF THE INVENTION

The present invention is directed to methods of finding maximal matches in data strings and for tin fling matches in parameterized strings, that is, strings containing symbols from more than one alphabet, in which the symbols from one of the alphabets are treated as parameters.

In accordance with one aspect of the invention, the problem of identifying non-exact matches in data strings is solved by identifying duplications of a parameterized pattern string in a parameterized text string by identifying relationships between symbols in the pattern string which are based on known pattern string information, and using those relationships to reduce the number of comparisons made between the pattern string and text string.

In preferred embodiments, at least one table is created which is based on known pattern string information and represents relationships between symbols in the pattern string. The relationships establish a lower bound which determines the number of consecutive positions to move a pattern pointer with respect to the text string. The pattern string is compared to the text string in a direction from right to left, starting at the right end of the pattern string. When a mismatch between the pattern string and the text string is detected, the pointer moves the pattern string a predetermined number of positions to the right to a point at which the pattern string at least partially matches the text string. The pattern string is shifted along the text string until a parameter match between the pattern string and text string is detected.

In accordance with another aspect of the invention, maximal matches are found by creating a suffix tree representing the data string, generating lists for each node in the tree indicating the left contexts of all suffixes associated with that node and reporting matches for pairs of suffixes having different left contexts.

In accordance with another aspect of the invention, parameterized matches are found by substituting a common symbol for the symbols of the alphabet representing the parameters before creating the suffix tree and then discarding matches found for which the actual parameters are not consistent.

In accordance with still another aspect of the invention, which is a preferred embodiment, integers are substituted for the symbols of the alphabet representing the parameters, such symbols being chosen to create a linked list in the data string for each different symbol in such alphabet. Matches found by the suffix tree are then consistent and no matches need be discarded.

Another aspect of the invention uses suffix trees in conjunction with square matrices to analyze data strings.

3

These and other aspects of the invention will become apparent from the drawings and detailed description.

BRIEF DESCRIPTION OF THE DRAWING

FIG. 10a–10d illustrate the matrix A of FIG. 6 divided into L-shapes characters and an L-string for the matrix derived from the L-shaped characters.

FIGS. 11a and 11b illustrate a matrix containing unique end-markers and an L-string representation of the matrix.

FIG. 12 illustrates an L-suffix tree of the matrix illustrated in FIG. 9a.

DETAILED DESCRIPTION

The present invention is directed to a method of identifying duplication in strings, such as coded structures. More particularly, the present invention is directed to identifying maximal matches in a string. Maximal matches are pairs of substrings which cannot be extended either to the left or to the right and which are preferably of at least a threshold length. Many times, however, the matches are parameterized matches in which each of a pair of substrings contains the same pattern of symbols except that certain symbols in one of the substrings are labeled differently, but are in the same position as other symbols within the second substring. In order to provide consistency and to avoid unnecessary duplication, it is necessary to be able to identify these parameterized matches.

FINDING MAXIMAL MATCHES IN A STRING

An efficient way to represent a data string S is by a suffix tree, which represents all of the suffixes of the string. A suffix of a string is a substring beginning at some position i in the string and continuing on to the end. In the preferred embodiment, the data string includes a unique endmarker ($), which does not occur elsewhere in S. In such a tree, arcs extend from a root through internal nodes to leaf nodes. Nodes which depend from a node are referred to as children. Each arc represents a portion of the string. At the root and each node, the label for each arc begins with a different symbol.

4

Each leaf represents a suffix, which can be read by concatenating the labels along the path from the root to the leaf.

Figure 1:
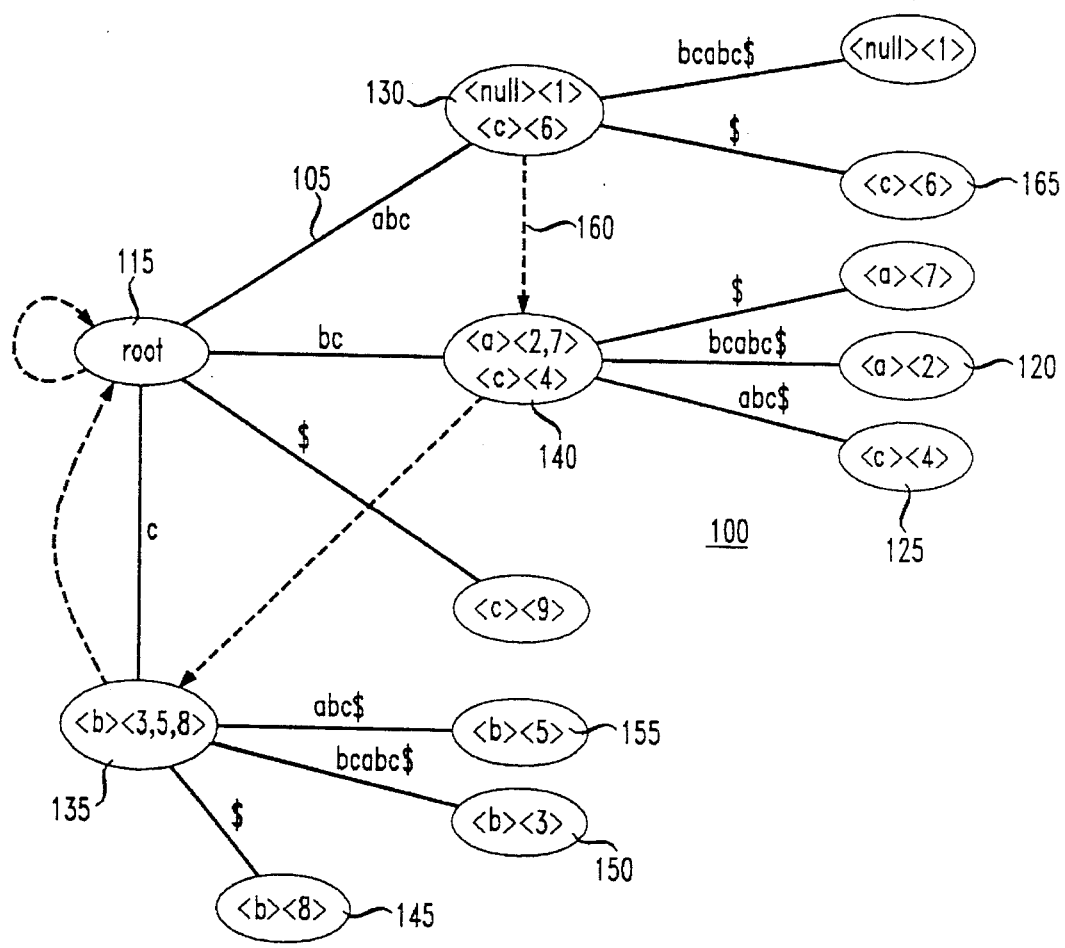
FIG. 1 illustrates a suffix tree for data string S.

FIG. 1 illustrates an example of a suffix tree 100 for a regular string S=abcbcabc$. In order to construct the tree, each suffix i of the string S must be identified. The suffixes of S are: abcbcabc$, bcbcabc$, cbcabc$, bcabc$, cabc$, abc$, bc$, c$, and $.

CONSTRUCTING A SUFFIX TREE

A suffix tree for a string can be represented by storing the string itself, along with information for each node in the tree. Such information can include items such as an identification of the node's parent, a pointer to the position in the string of the beginning of the arc leading to the node, the length of such arc, the pathlength from the root to the node and a suffix link. Suffix links are pointers to other nodes, which, as described by McCreight, speed up the creation of suffix trees by eliminating the need to return to the root each time a new suffix is added to the tree. Suffix links also aid in searches through trees. In general, the suffix link for a node having pathstring (Si . . . Sj) points to the node having pathstring (Si+1 . . . Sj). In FIG. 1, suffix links are indicated by dotted arrows. For example, as indicated by dotted arrow 160 in FIG. 1, the suffix link for node 130, whose pathstring is "abc," points to node 140, whose pathstring is "bc."

It is not always possible to determine the suffix link for a node when the node is created because the destination node for the suffix link may not have been created yet. For example, node 140 is created (by addition of leaf node 125) before node 135 (by addition of leaf node 155). However, node 140 exists when node 130 is created (by addition of leaf node 165). When a node is created, its identity typically becomes the suffix link for the previous node created.

Figure 2:
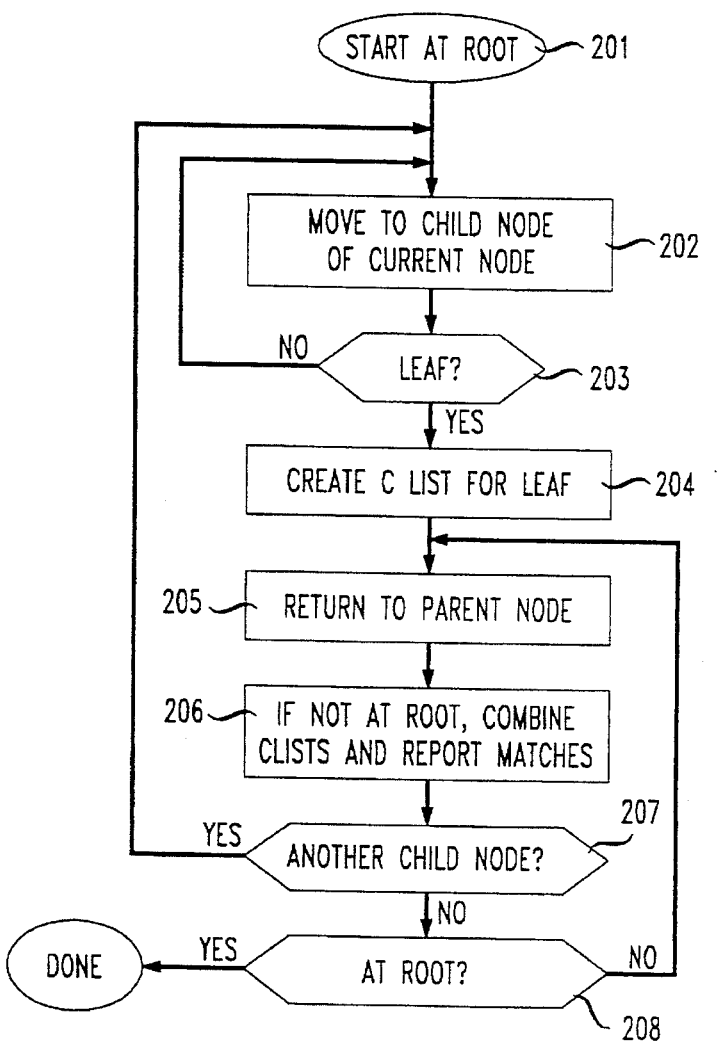
FIG. 2 illustrates a flow chart depicting a method of identifying maximal matches.

FIG. 2 is a flow chart showing the steps in identifying maximal parameter matches in a string for which a suffix tree has been created. As will be described, a data structure called a plist is constructed for each node in the suffix tree. For each leaf node, the plist is a pair of the form:

<left context><position> where <position> is the position in the string where the substring represented by the leaf node begins and <left context> is the symbol just to the left of such position. For example, in FIG. 1, the plist for leaf node 120 has left context "a" and position "2" and the plist for leaf node 125 has left context "c" and position "4".

The clist for each internal node is one or more plists of the form:

<left context><set of positions> which combines the plists from all children of such node. In performing such combination, it is convenient to compress the data structure by combining plists having the same left context. The plists for internal node 130 cannot be so compressed because the left context for both children are different. In contrast, the plists for node 135 can be compressed into a single entry because the left context for the children of node 135 are all the same. The clist for node 140 requires two entries for two different left contexts "a" and "c".

Node 130 is at a length of 3 symbols from the root, and the fact that such node has two children indicates a match of two substrings of at least that length. Since there is more than one plist in the clist for such node, such match is maximal length. As can be seen from string S, the symbols "abc" are repeated. However, in the clist for node 135, all entries have the same left context, so there are no maximal matches indicated.

As a slightly more complicated example, consider a tree (not shown) having a node at length 10 from the root with the following clist:

<a><10, 70>

<b><30, 50>

This clist indicates four maximal matches of length 10, that is, the substring beginning at position 10 matches substrings beginning at positions 30 and 50 and the substring beginning at position 70 also matches substrings beginning at positions 30 and 50. The strings beginning at positions 10 and 70 also match each other, but the match is not maximal because such strings have the same left context "a". Similarly, the match of the string beginning at positions 30 and 50 is not maximal.

Maximal matches can thus be determined from clists. Clists can be created by the process shown in FIG. 2. In general, the process recursively finds the plist for each leaf node and then the combined clists for each internal node. Maximal matches having a length over a preset threshold are determined from the clists.

The process shown in FIG. 2 begins at the root node (step 201), and moves to a child node of that node (step 202). If such child node is not a leaf node (step 203), the process repeats step 202 until a leaf node is reached. Then a plist having a left context and a position is determined for such leaf node. For example, referring back to FIG. 1, beginning at root node 105, the process might first move to internal node 135 and then to leaf node 145 to calculate the plist for leaf node 145.

After the plist for the leaf node is determined, the process returns to the parent node(step 205), combines the plist just created with other plists created for such node, and reports any maximal matches found (step 206). Of course, on the first return to such parent node, only one plist will have been created, so no combination is possible and no matches will be found. If another child node exists leading from such parent node, the process repeats steps 102, 103, 104, 105, and 106 for each additional child node. Again referring to FIG. 1, the process creates the plist for leaf node 150, combines that plist with that created for node 145, then creates the plist for leaf node 155 and combines that plist with the previous combination. However, since the resulting clist for internal node 135 has only one entry, no match is indicated.

If there is no other child node (step 207) and the node being addressed is not the root (step 208), then the process returns to step 105 to address the next parent node in the path to the root. If the new parent node is not the root, step 106 is performed for the new parent node to combine clists and detect matches. However, for tree 100 in FIG. 1, such return from internal node 135 is to root 215, so the plists are not combined.

In general, the process repeats the above steps until all nodes in the entire tree have been traversed and clists for all leaves have been created and combined for each internal node. When a clist contains more than one entry, maximal matches are reported if the matches exceed the minimum length desired. For example, for tree 100 in FIG. 1, the clist for internal node 140 indicates maximal matches for 2-symbol substring "bc" at positions 2 and 7 with the substring at position 4 and the clist for internal node 130 indicates a maximal match for 3-symbol substring "abc" at the beginning of the string and at position 6. If the minimum length desired is 3 symbols, then the match indicated by the clist for node 130 would be reported but the matches indicated by the clist for node 140 would not.

PARAMETERIZED STRINGS (P-STRINGS)

A parameterized string (p-string) S comprises a plurality of symbols, at least one of which is a parameter. An example of a pair of p-strings $S_1$ and $S_2$ are as follows:

$$S_1 = axaybxycby \quad (1)$$

$$S_2 = ayavbyvcbv \quad (2)$$

Each p-string $S_1$, $S_2$ contains a plurality of symbols from a first alphabet ($\Sigma$) and a second alphabet ($\Pi$) both of which are preferably finite. The symbols in the first alphabet can be ordinary or non-parameter symbols and the symbols in the second alphabet can be parameter symbols. The p-strings can comprise symbols from any number of types of alphabets. In the present example, $\Sigma = \{a,b,c\}$ and $\Pi = \{x,y,v\}$.

A parameterized match (p-match) exists between two strings if one p-string can be transformed into the other p-string by consistently renaming the parameters from one p-string to the other. In determining whether two p-strings are a p-match, each of the p-strings is scanned from left to right. At the same time, a table is constructed which provides a one-to one correspondence between symbols in each string to determine if any mismatches are found between the symbols.

For example, below p-strings $S_1$ and $S_2$ are shown in a table format which illustrates the one-to-one relationship between symbols of corresponding position in each p-string.

| # | $S_1$ | $S_2$ |
|---|-------|-------|
| 0 | a | a |
| 1 | x | y |
| 2 | a | a |
| 3 | y | v |
| 4 | b | b |
| 5 | x | y |
| 6 | y | v |
| 7 | c | c |
| 8 | b | b |
| 9 | y | v |

The first column of the: table indicates the position from left to right of each symbol in the string, starting with symbol 0. The second and third columns list the symbols in p-string $S_1$ and p-string $S_2$. As can be seen, symbols from alphabet $\Sigma$ in the first p-string $S_1$ are in the same position and are of the same type as those corresponding $\Sigma$ symbols in p-string $S_2$. More explicitly, symbol a in p-strings $S_1$ and $S_2$ occurs at positions 0 and 2, symbol b in p-strings $S_1$ and $S_2$ occurs at positions 4 and 8 and symbol c occurs at position 7.

With respect to the parameter symbols from alphabet $\Sigma$, symbol x in p-string $S_1$ and symbol y in p-string $S_2$ occur at the same positions, i.e., positions 1 and 5, and symbol y in p-string $S_1$ and symbol v in p-string $S_2$ occur at the same positions, i.e., 3, 6 and 9. Essentially, symbols x and y in p-string $S_1$ have been renamed y and v in p-string $S_2$. Therefore, since all like symbols from the first alphabet in p-strings $S_1$ and $S_2$ are in the same positions, and all like symbols from the second alphabet are in the same corresponding positions as like symbols in p-string $S_2$ which are different from the like symbols in p-string $S_1$, a parameterized match exists between p-strings $S_1$ and $S_2$. By examining the p-strings in a table format, not only can mismatches in length be detected, but also mismatches between different non-parameters, differences between a parameter and a non-parameter, or between two parameters where at least one of the parameters has already been made to correspond to a different parameter. The detection of mismatches in this manner can be done in time linear with respect to the strings being matched.

FINDING MAXIMAL MATCHES IN PARAMETER STRINGS

Figure 3:
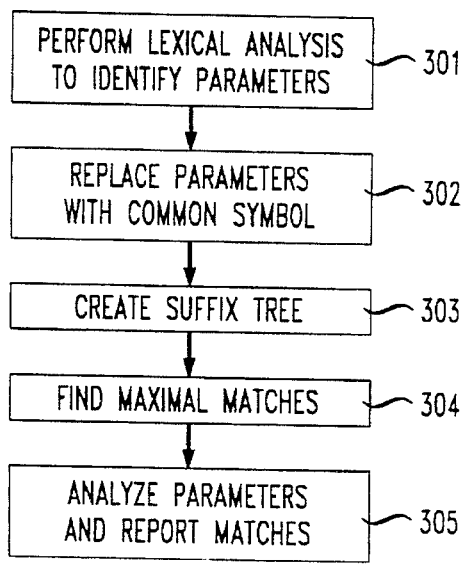
FIG. 3 illustrates a flow chart depicting a method of identifying maximal parameter matches.

Because of the complexity of identifying repetitions of different parameters within a string, parameters can be labeled by the same identifier so that the parameterized string is simplified. FIG. 3 is a flow chart representing one method of identifying maximal parameterized matches.

A data string, such as computer code, including parameters is first subjected to a lexical analysis in which parameters are identified (step 301) and encoded by replacing each parameter with a common symbol (step 302). Techniques for performing the lexical analysis are disclosed in A. V. Aho, el. al., Compilers: Principles, Techniques and Tools, Addison-Wesley, Reading, Mass., 1986.

For example, lexical analyses of a parameterized string x=fun(y)+3* x and replacement of each parameter with the symbol "p" generates the following output: p=p(p)+p*p and a parameter list x, fun, y, 3, x. String axaybxycby using alphabets Σ and Π yields apapbppcbp and parameter list x,y,x,y,y. A matching step can then match strings with the same numbers and positions of symbols.

Next, a suffix tree is created (step 303) and a sequence matching process is performed in the same manner as described above to find all maximal parameterized matches in the text that are at least as long as a predetermined threshold length. Then the actual parameters for each match are analyzed (step 305) to determine if an appropriate one-to-one correspondence can be made. The matches for which such correspondence exists and all other matches are discarded.

Figure 4:
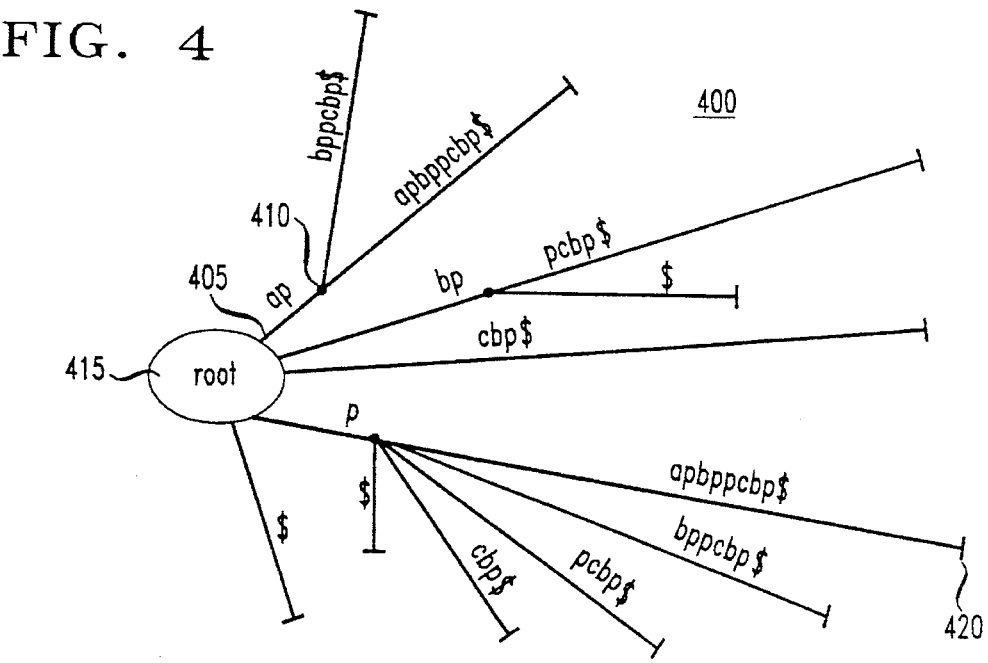
FIG. 4 illustrates a suffix tree for an encoded string S(P).

Suffix tree 400 for the encoded version of a string is illustrated in FIG. 4. If either string $S_1$ or $S_2$ is encoded as described above, the following string results:

$$S(p)=apapbppcbp\$ \qquad (3)$$

The suffixes of S(p) are as follows: apapbppcbp$, papbppcbp$, apbppcbp$, pbppcbp$, bppcbp$, ppcbp$, pcbp$, cbp$, bp$, p$ and $. Each arc of suffix tree represents a substring of the input string S(p).

Once the suffix tree is constructed, it can be used to identify parameterized matches in the string, as described above.

When a match is found between two substrings in a parameterized string, the actual parameters in the substrings must then be compared to determine the extent of the match in the parameters themselves. This can be accomplished by rewriting the parameters in one substring to match the parameters in the other until a conflict occurs. For example, if the matching substring is apbpcp . . . , (where "p" indicates a parameter) and the actual substrings are axbycy . . . and arbsct . . . ; then in the rewriting x becomes r and y becomes s, but then y cannot also become t. If such a conflict exists, then the match can be reported as shorter matches that exceed the predefined minimum. In the above example, the match of axby and arbs would be reported, then the analysis would be restarted with y becoming t.

As another example, the following two sequences of computer code are analyzed:

| Line | Seq1 | Seq2 | Comparison |
|---|---|---|---|
| 1 | x = y + z | x = a + b; | x → x; y → a; x → b |
| 2 | if (y > z) | if (b > c) | y → b; z → c |

-continued

| Line | Seq1 | Seq2 | Comparison |
|---|---|---|---|
| 3 | print ("yes"); | print ("no"); | "yes" → "no" |
| 4 | h = f(x); | h = f(x); | h → h; x → x |
| 5 | y = x; | c = x; | y → y; x → x |

A conflict exists in line 2 because y→a in line 1 and y→b in line 2. As such, a match can be reported of just one line. It is to be understood, however, that in practice a match less than a predetermined threshold would not be reported. The parameter analysis can be restarted on line 2, the line just after the conflicting parameter use. A second conflict is introduced on line 5, and a match can be reported for lines 2–4. Finally, a third match can be reported for line 5.

"PREV" FUNCTION

A problem with tile parameterized matching process described above is that much computation time can be wasted in finding matches that are later discarded during parameter analysis. A solution in accordance with the present invention is to use a dynamic encoding process for chaining together occurrences of the same parameter within a string.

Figure 5:
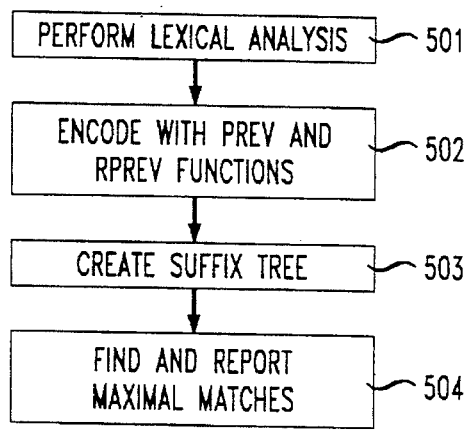
FIG. 5 illustrates a flow chart depicting a method of identifying maximal parameter matches in a parameter string encoded by the prev function.

FIG. 5 shows a preferred, more efficient process for finding matches in a parameterized string. First, the lexical analysis is performed as described above (step 501 ). Then, the resulting string is encoded with a "prev" function as described in further detail below to substitute integers for the parameters (step 502). A suffix tree is then constructed from the encoded string (step 503) and matching sequences are found by creating clists for the internal nodes in the suffix tree and using clists to find and report matches that exceed the desired threshold (step 504). Because of the use of the "prev" function, the matches found will be true matches and it is not necessary to analyze the parameters as in step 305. However, the steps of creating a suffix tree and finding matches are different for a string encoded with the prev function, as will be described below.

The prev function is a dynamic encoding scheme for chaining together occurrences of the same parameter within a p-string. For example, the prev function replaces the parameters in p-string S with integers as follows:

$$S=axaybxycby$$

$$prev(S)=a0a0b43cb3 \qquad (4)$$

The prev function establishes a relationship between each parameter in the p-string, other parameters of the same type and an initial reference position. In the preferred embodiment, the leftmost occurrence of a parameter is represented by a "0", and each successive occurrence is represented by an integer indicating the difference in position compared to the previous occurrence of the same parameter. Such integers are called parameter pointers. In the case of p-string S, each parameter pointer is represented by a single digit. However, in strings where occurrences of the same parameter are more widely separated in the string, multi-digit integers may be needed for pointers.

The suffixes for a p-string encoded with the prey function are also encoded with the prey function, the p-suffixes for prev(S) are illustrated below:

| a | 0 | a | 0 | b | 4 | 3 | c | b | 3 | $ |
|---|---|---|---|---|---|---|---|---|---|---|
|   | 0 | a | 0 | b | 4 | 3 | c | b | 3 | $ |
|   |   | a | 0 | b | 0 | 3 | c | b | 3 | $ |
|   |   |   | 0 | b | 0 | 3 | c | b | 3 | $ |

|   |   |   |   |   |   |   |
|---|---|---|---|---|---|---|
| b | 0 | 0 | c | b | 3 | $ |
|   | 0 | 0 | c | b | 3 | $ |
|   |   | 0 | c | b | 3 | $ |
|   |   |   | c | b | 0 | $ |
|   |   |   |   | b | 0 | $ |
|   |   |   |   |   | 0 | $ |

As can be seen, the number of p-suffixes associated with prev(S) are equal to the number of symbols in prev(S). The p-suffixes derived can then be represented by a parameterized suffix tree (p-suffix tree) as described hereinafter.

A suffix for a regular string can be determined from the string by reading the suffix from its beginning position in the string. Such procedure can also be used for a p-string encoded with the prev function except when a pointer is encountered. As can be seen from the above table of suffixes for prev(S), pointers change as the parameter positions to which they point are truncated. A "transform" function can be used to perform this change. Accordingly, "transform (b,j)" is defined as follows: If b is an integer greater than j−1, replace b with 0.

When used on pointers to determine a p-suffix from a stored string prev(S), b is the pointer and j is the position of the pointer in the p-suffix. Such function can also be used in a different manner for finding left contexts, as will be described below.

PARAMETERIZED SUFFIX TREE

Figure 6:
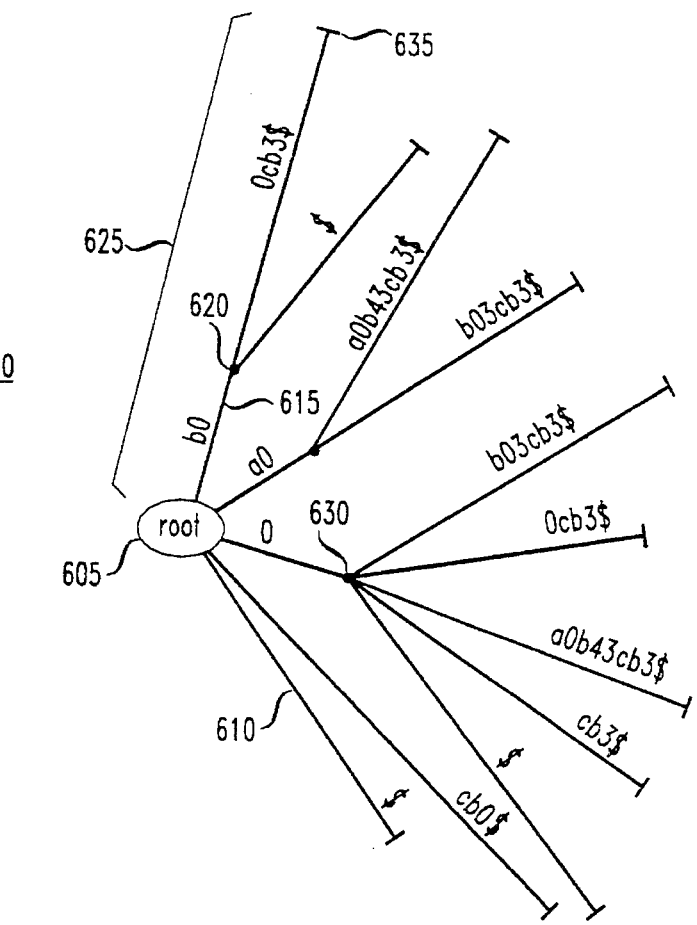
FIG. 6 illustrates a parameterized suffix tree of prev($S_1$) string in accordance with the present invention.

FIG. 6 illustrates a p-suffix tree 600 for the p-string S. The tree comprises a root 605 from which extends a plurality of arcs 610 which are each labeled with a non-empty substring of the input p-string S. For example, suffix b00cb3$ comprises a first arc 615 labeled by substring b0 and a second arc 620 labeled by substring 0cb3$. The combined substring comprising the first and second arcs is referred to as a path string 625. The path string formed by the sequence of arcs which originates at the root 605 and ends at a leaf node, 635 represents a single suffix. A prefix is the first part of a string or p-string, from the first symbol to symbol i, where $1 \leq i \leq n$ and n is the length of the string of p-string. For example, the label of the first arc 615 is a prefix of suffixes b0$ and b00cb3$.

Internal nodes 630 exist where there are common prefixes for different p-suffixes of the p-string. Each internal node 630 has at least two arcs extending therefrom, each beginning with a distinct symbol. Each node includes a pathstring which is a sequence of symbols existing in a path from the root to that particular node. The number of symbols within the pathstring is referred to as the pathlength. For each leaf, the pathstring is a distinct p-suffix. Therefore for a given p-string of length n, the number of leaves within the tree is n and the number of nodes in the tree is linear in n. The number of symbols in p-string S including the endmarker is 11. Referring to FIG. 6, it can be seen that the number of leaves in the p-suffix tree for p-string S is also 11.

CONSTRUCTING A P-SUFFIX TREE

Suffix links for a pstring encoded with the prev function need special consideration. The creation of a suffix tree involves inserting an internal node for each suffix added to the tree at the point where that suffix differs from suffixes previously in the tree. Thus, up to a given node, the suffixes depending from such node share a common portion and differ beyond the node.

Regular strings have two properties on which the ability to create suffix links depends, the common prefix property and the distinct right context property. The common prefix property is the property of two matching strings that the strings will still match if the first symbol of each string is removed. The distinct right context property is the property of two matching strings that if two strings differ because of the last symbol, the strings will still differ if the first symbol of each string is removed.

However, while strings encoded with the prey function follow the common prefix property, they do not follow the distinct right context property. The effect is that, in using the tree creation methods described above, the correct nodes may not always be created for suffix links to point to. In such a case, the suffix link for a node being created can be defined to point to a node in the tree having a pathstring as close as possible to that of the desired node.

Suffix links pointing to desired nodes can be marked as "good" suffix links and those pointing to close-by nodes can be marked as "bad" suffix links. Then, when a "bad" suffix link is used as a pointer, a rescanning step can be added to move up or down in the tree from the node indicated by the "bad" suffix link to find the exact position where the next node is to be created. When the node is actually created, the "bad" suffix link can then be updated to point to the correct node. In the preferred embodiment, each "bad" suffix link is defined to point to a node N in the tree beyond the desired node position and the rescanning step finds the correct position in the arc leading from node N to its parent.

IDENTIFYING MAXIMAL P-MATCHES OF A THRESHOLD LENGTH

Strings $S_1$ and $S_2$ are a p-match if prev($S_1$) is the same as prey($S_2$). For example, if $S_1$ is abxyaycx and $S_2$ is abzxaxcz, then prev($S_1$)=ab00a2c5=prev($S_2$). Here, x,y,z are parameters and a,b,c are nonparameters.

Now, suppose that $S_1$ and $S_2$ are a p-match and both are part of a longer p-string S. If $S_1$ starts at position i, $S_2$ starts at position j and $S_1$ and $S_2$ have length n, then S is said to have a p-match of length n starting at positions i and j. More succinctly, S may be said to have a p-match (i,j,n). For example, using $S_1$ and $S_2$ as defined in the last example, if S=bxabxyaycxczabzxaxczbca, then $S_1$ is the substring starting at position 3, $S_2$ is the substring starting at position 13, and S has a p-match (3, 13, 8).

It may be possible, however, that when S has a p-match (i,j,n), S may also have a p-match (i−1, j−1, n+1) if the p-strings of length n starting at positions i and j are a p-match; such a p-match is said to be left-extensible. In our example, S also has a p-match (2, 12, 9). Thus, the p-match (3, 13, 8) can be extended by one position to the left. The p-match (3, 13, 8) is thus left-extensible. Similarly, examples could be constructed of p-matches that can be extended by one position to the right; such p-matches are called right-extensible.

If a p-match can be extended to the left or right, it would be most useful not to report it separately, as the longer p-match will be reported as well. Therefore, it is useful to define maximal p-matches as those p-matches that are neither left-extensible nor right-extensible. The p-match (2, 12, 9) in the above example is maximal because it cannot be extended to the left (because position 1 contains a b while position 11 contains a c) and it cannot be extended to the right (because position 11 contains a c while position 21 contains a b).

Determining whether a p-match (i, j, k) of a p-string S is right-extensible is easily determined by comparing p-suffix i and p-suffix j: if they are the same for k+1 symbols, then the p-match is right-extensible, while if they differ at the (k+1)st symbol, the p-match is not right-extensible.

However, whether p-match (i, j, k) is left-extensible cannot be determined simply by comparing the symbols of S or prev(S) in positions i−1 and j−1 or even the first symbols of p-suffix i−1 and j−1. The reason is that the value of a parameter pointer depends on preceding context.

For example, if two p-suffixes have a common header, a "0" in the header could mean different things in each p-suffix. In one p-suffix, the "0" could have replaced a pointer to the symbol immediately preceding the p-suffix; in the other it could have replaced a pointer to an earlier symbol in the p-string.

One way to identify left extensibility is to construct another string rprev(S), which is similar to prev(S) except that the pointers are determined in the reverse direction. For example:

S=axaybxycby$ prev(S)=a0a0b43cb3$ rprev(S)=a4a3b03cb0$

The string rprev(S) is then used When finding a left context to determine left-extensibility.

In finding a left context in a p-string encoded with rprev(S), the "transform (b,j)" function described above is needed to modify pointers. In this use of the transform, b is the pointer being modified and j=n+1, where n is the pathlength of the node for which the left context is being determined. Thus, the left context of a p-suffix with respect to a particular node can be found.

As an example, suppose that a node N has children N1, N2, . . . , Nk, from left to right, and pathlength n. If two leaves corresponding to p-suffixes m and t, respectively, are taken from the subtrees of Ni and Nj, where i=j, then (m,t,n) is a p-match that is not right-extensible, since p-suffixes m and t agree for n symbols, and then disagree at the (n+1)st symbol. If the transformed left contexts for p-suffixes m and t are also different, i.e. the symbols of rprev(S) at positions m−1 and t−1 are different, then the p-match is not left-extensible, and the p-match is maximal. For example, consider FIG. 6, which illustrates the p-suffix tree for prev(S)= a0a0b43cb$, for which rprev=a4a3b03cb0$. There is a p-match (6, 7, 1) which corresponds to a pathstring of a single symbol 0 in the p-suffix tree for node 630 in the tree; this p-match is not right-extensible because the leaf for p-suffix 6 is reached through the arc of node 630 whose label begins with 0, while the leaf for p-suffix 7 is reached through the arc whose label begins with c. This p-match is not left-extensible because the 5th symbol of rprev(S) is b while the 6th symbol is 0, and transform (0, 2)=0.

Plists and clists can thus be generated for "prev(S)" strings using a method similar to that described above for regular strings, but with the "rprev(S)" string and "transform (b, j)" function being used in finding left contexts and other modifications as will now be described.

In general, the method classifies the leaves in the subtree subtree rooted at each child of a node N according to the left Context transformed with respect to N. For example, if leaf L1 is for p-suffix 3 with transformed left context 0, leaf L2 is for p-suffix 10 with transformed left context b, and leaf L3 is for p-suffix 7 with transformed left context 0, L1 and L3 would be grouped under 0 and L2 would be under b. Thus, there would be one plist 0:3,7 and another plist b:10.

Thus, a method for finding all maximal p-matches is to do the following for each node N: find all leaves L1 and L2 corresponding to p-suffixes r and s, respectively, such that the transformed left context (with respect to N) of r and s are different and L1 and L2 belong to the subtrees of different children of N, and for each such pair of leaves, report a p-match (r,s,n), where n is the pathlength of N. This can be accomplished by doing the following for each N: sort the leaves of each subtree rooted at a child of N into plists, where each plist corresponds to a distinct transformed left context with respect to N, and then for all pairs Ni and Nj, with i≦j, consider all pairs of plists Bi and Bj where Bi is a plist for Ni and Bj is a plist for Nj, and for each such Bi and Bj that correspond to different transformed left contexts with respect to N, and each m in Bi and each t in Bj, report a maximal p-match (m,t,n).

Because a leaf rooted at a child node Ni may have a transformed left context that is nonzero at Ni but zero at its parent node N, the entry for such a leaf can appear in different plists in Ni and N. Thus, leaves represented in separate plists with different nonzero integers as left contexts in node Ni can be represented in the plist with "0" as left context in node N. An example is a left context that is "3" when evaluated as transform (3,4) at a node of pathlength 3 but "0" when evaluated as transform (3,3) at a node of pathlength 2. Thus, for prey(S) strings, when the clists are processed at a node, the left contexts are always determined with respect to the pathlength of the node so that the pointers will be correct.

It is not necessary to create clists for nodes having pathlengths less than the minimum match desired, as such clists will not be used.

PATTERN MATCHING

The present invention is also directed to a method of finding all occurrences of a pattern P in a text string T by means of a suffix tree for P augmented with suffix links. The basic idea for strings is to follow the path determined by symbols of T through the tree, starting at the root and the first symbol of T. Whenever the next symbol of T is not available in the tree, follow the suffix link from the last node reached, rescan downward using arc lengths to catch up to the last symbol of T already matched, and continue following the path downward determined by symbols of T. Whenever the current position in the tree corresponds to matching the last symbol of P before the endmarker, a match is reported.

In the ith stage, $1 \leq i \leq T$, A comparison is made between the ith p-suffix of T and the p-suffixes of S. For i=1, the N-root, and len-1 are initialized; in general, at the start of a stage, N represents the node to begin searching from, and len represents the pathlength corresponding to the next text symbol that needs matching. In Stage i, this will be symbol $T_{i+len-1}$; the pathstring prev $(T_i \ldots T_{i+len-2})$ terminates either on the arc from parent(N) to N or below N. In the latter case, rescanning of $T_i \ldots T_{i+len-2}$ by comparing the first symbols of arcs to the text symbols (transformed by f) is used to get to a point in the tree corresponding to pathstring prev($T_i \ldots T_{i+len-2}$) and pathlength len-1. Starting with j=len, the algorithm tries for successive values of j to match the transformed jth symbol of the ith p-suffix to T to a symbol at pathlength j in the tree; the transformed jth symbol is f(prev(T)[i+j−1],), where f is as defined in Section 2. Thus, a path is followed downward in the tree, matching transformed input symbols against symbols in the pathstring. If it passes through the symbol corresponding to the last symbol of P (not counting the endmarker), a p-match is reported. When the jth symbol of the ith p-suffix of T is not available in the tree, no longer prefix of this p-suffix matches any prefix of a p-suffix of P. In this case, if a node at pathlength j−1 is reached it is referred to as $\bar{N}$; otherwise let $\bar{N}$ be the parent of the node reached by the arc currently being examined. Set N=SL($\bar{N}$) and increment i; if j−1, set len=j, and otherwise, set len=j−1.

Another way to find occurrences of string P in string T is to append P to T and search for matches by using clists as described above. Each match of P found in T will then be reported.

Figure 7:
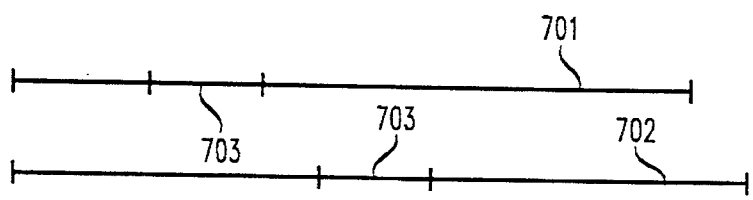
FIG. 7 shows two strings of text to be compared for common text.

Two strings of comparable length Can be compared by concatenating the two strings and then searching for matches in the combined string by using clists. It may be desirable to eliminate duplicate substrings in each string first before concatenation to minimize the length of the combined string. For example, in FIG. 7, two text strings 701 and 702 are represented. Text portion 703 is present in both strings 701 and 702. If strings 701 and 702 are concatenated to form one long string and a search made for matches, the duplication of text portion 703 will be reported. This method can be used, for example, in finding plagiarized text by concatenating a suspected text onto the text believed to be plagiarized. Clearly, all these procedures for finding occurrences of one string in another and comparing strings can be performed for parameterized strings by using the methods of the invention described above.

Figure 13:
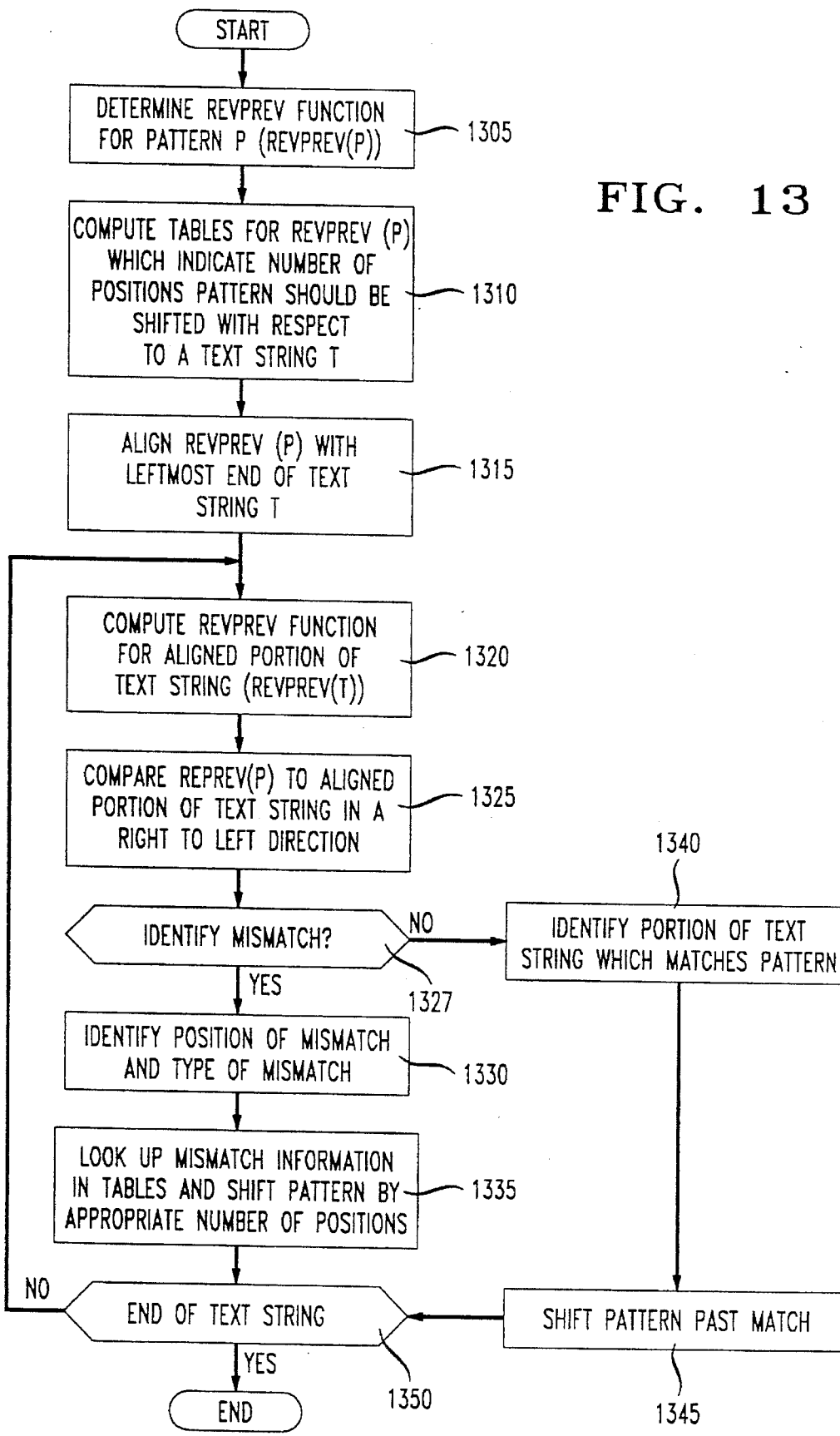
FIG. 13 illustrates a flow chart depicting an alternative method of identifying maximal parameter matches in a text string.

FIG. 13 illustrates a flow chart depicting an alternative embodiment for identifying occurrences of a pattern P in a text string T. The revprev function defined above is computed for the pattern P (referred to as revprev(P)) (step 1305). Next, tables are computed from revprev(P) which determine the number of positions the pattern P will be shifted relative to a text string T based on the position and the type of mismatch identified when the encoded pattern string and text string are compared (step 1310). The revprev function for the text string T is computed on the fly, i.e., the value is computed for each symbol just before it is compared with a pattern symbol. Alternatively, the revprev function for the aligned portion of the text string can be computed just prior to its comparison with the pattern string.

The encoded pattern P is then aligned with the text string T starting at the left-most end of the string (1315). The revprev function is computed for each symbol of the aligned portion of the text string T just prior to comparison with a pattern symbol (step 1320). The encoded pattern P is compared to the encoded portion of the text string in a right to left direction. Comparison of pattern characters to text characters which have been encoded using the revprev function continue until a match of the entire pattern is identified or until a mismatch is identified (step 1325). When a mismatch is found, the position of the mismatch and the type of mismatch are identified with respect to the encoded pattern (step 1330).

For example, the type of mismatch can include a mismatch between two constant characters, a mismatch between a constant and a parameter or a mismatch between two parameters. Once the mismatch information is determined, the information for determining the number of positions that the pattern should be shifted is found in one of the precomputed tables (step 1335). If no mismatch occurs, then a pattern match is identified (step 1340). In either case, the pattern is realigned with the text string and steps 1320–1340 are repeated until the pattern is aligned with the end of the text string.

Unlike a regular text string, the encoded characters in the parameterized pattern and text string cannot be compared in isolation but must be considered with respect to the relative positions of other encoded characters contained in the pattern or text string. Each parameter character contained in the pattern string P represents a place holder for an actual parameter character contained in text string T. Each place holder of a particular parameter designation, i.e., parameter name, is bound by an actual parameter character in an aligned portion of the text string once a pairing between the particular parameter designation and actual parameter character occurs. For example, if a parameter designation B in the pattern is initially aligned with a parameter Z in the text, the pairing of B and Z are bound for that aligned portion of the text. As such, if B is also aligned with Y, a mismatch will be detected. The binding of an actual parameter to a particular parameter designation occurs at each aligned portion of the text. Therefore, if B and z are bound in one aligned portion of the text, B may be bound to Y in another aligned portion of the text. As such, when a mismatch is detected, it is important that both the position of the mismatch and the type of mismatch are taken into consideration. Such consideration is more clearly seen with reference to the example described below.

A pattern P=ZYaaYaY is compared to a text string T= aaBaZaBaaCbBCaaCaCaBaaB, where upper case letters represent parameter characters and lower case letters represent constant characters, to determine how many occurrences of the encoded pattern P occur in the text string T. As described above, first the revprev function is computed for the pattern P. In determining the revprev function, the order of P is reversed, the prev function is computed on the reversed string and then the order of the prev encoded string is reversed so that revprev=03aa2a0. The revprev function for the text string T is determined on the fly for the portions of the text string which are aligned with and being compared to the encoded pattern P as is illustrated below. The revprev function for the text can be computed using any known method such as, but not limited to, using lists, balanced trees or hashing. Each time the encoded pattern P is shifted along the text string T, the revprev function is recomputed for each symbol of the portion of the text string being directly compared to the pattern.

Next, tables are precomputed for the encoded pattern P. In accordance with the present example, three tables are computed for the pattern P. Each of the tables indicates the number of positions the text pointer should be shifted to the right in text string T when a mismatch occurs between the encoded pattern and text string. The encoded pattern P will also be shifted to the right to align its rightmost character with the new position of the text pointer. It is to be understood that future reference to the shifting of the text pointer implicitly includes a corresponding shifting of the position of the encoded pattern string P with respect to the text string T which results in the rightmost symbol of the encoded pattern string P being aligned with the text pointer.

The first table determines the number of positions the text pointer is shifted when a mismatch occurs between the encoded text string and the encoded pattern in which a mismatched encoded character k in the encoded aligned portion of the text string T is not equal to zero and further is contained in the encoded pattern P. The pattern is shifted so that an encoded character k contained in the pattern is aligned with the encoded character k in the text string. If the mismatched encoded character k is not contained in the pattern, the pattern is shifted so that the left-most end of the pattern is shifted one position to the right of the encoded character k. In the present example, a number 7 indicates that the specific character does not occur in the encoded pattern string and causes the pattern to be shifted beyond the point of mismatch. The pattern is preferably shifted past the mismatch by the minimum amount. As shown below, the first table (T1) for the encoded pattern P is computed as follows:

| T1 | |
|---|---|
| T1 [character] = | No. positions of shift of text pointer |
| T1[1] = | 7 |
| T1[2] = | 2 |
| T1[3] = | 5 |
| T1[4] = | T1[5] = T1 [6] = 7 |
| T1[a] = | 1 |
| T1[b] = | 7 |

The table T1 is computed for each position number corresponding to a position in the pattern and each constant character contained in the alphabet. As such T1[c]–T1[z] are all equal to 7 because they do not occur in the pattern.

The second table T2 indicates the amount by which the text pointer must be shifted when a mismatch occurs between the encoded text string and the pattern in which the mismatched encoded character k in the encoded aligned text string is equal to zero. For a position j in the pattern, the table T2[j] is computed from the position of the right-most occurrence of a symbol in the encoded pattern which is to the left of the point of the mismatch and is either zero or larger than m-j, where m is equal to the pattern length. For example, if m is 7, T2[2] would be based on finding either a zero or a symbol larger than 5 to the left of position 2 in the encoded pattern. The actual value of T2[2] represents the amount by which the text pointer should shift so that the resulting pattern shift aligns the identified symbol with the mismatched encoded symbol. Referring to the table below, this results in a text pointer shift of six positions. If no symbol to the left of the mismatched symbol is equal to zero or greater than 5, the pattern is shifted so that the left most end of the pattern is shifted one position to the right of the mismatched symbol. Table T2 for the encoded pattern P is computed as follows:

| T2 | |
|---|---|
| T2 [position] | No. positions of shift of text pointer |
| T2[1] = | 7 |
| T2[2] = | 6 |
| T2[3] = | 6 |
| T2[4] = | 6 |
| T2[5] = | 5 |
| T2[6] = | 2 |
| T2[7] = | 2 |

A third table T3 is determined which identifies the right-most portion of the encoded pattern which matches the rightmost portion of the aligned encoded text string and determines the number of positions to shift the text pointer so that the portion of the shifted encoded pattern aligned with the previously matched rightmost portion of the aligned text string will match that part of the text string. In determining the amount by which the pattern is shifted, the substring of the pattern which matches the substring of the text string must also exist in another part of the pattern and, therefore, the amount of the shift can be determined by the pattern alone. In addition, the match between the two substrings of the pattern should not be capable of being extended by an additional symbol to the left of the two matching substrings. Table T3 for the pattern P is computed as follows:

| T3 | |
|---|---|
| T3 [position] = | No. positions of shift of text pointer |
| T3[0] = | 13 |
| T3[1] = | 12 |
| T3[2] = | 11 |
| T3[3] = | 10 |
| T3[4] = | 9 |
| T3[5] = | 4 |
| T3[6] = | 6 |
| T3[7] = | 1 |

After the tables T1, T2 and T3 have been computed for the encoded pattern P, the pattern is aligned with the left-most end of the text string T. Typically, the third table T3 and one of the other tables T1 and T2 are used to determine the number of positions to shift the text pointer once a mismatch is identified. The table which produces the largest shift is used to determine the number of positions to shift the pattern. The pattern P is initially aligned with the left-most portion of the text string T as shown:

| position | 1234567 |
|---|---|
| P: | ZYaaYaY |
| T: | aaBaZaBaaCbBCaaCaCaBaaB |

The aligned encoded portions of P and T are as follows:

| position | 1234567 |
|---|---|
| revprev(P) | 03aa2a0 |
| revprev(T) | aa4a0a0 . . . |

Next, the revprev(P) is compared to revprev(T) in a right to left direction. A mismatch between the revprev(P) and the revprev(T) is identified at position 5 (T2[5]). Since the mismatched character k in the revprev(T) is zero, table T2 is referenced to determine the number of positions by which the text pointer should be shifted. In addition, table T3 is referenced to determine the number of positions to shift the text pointer so that the revprev(P) will match the a0 of revprev(T) (T3[5]). By referring to table T2, it is seen that the text pointer must be shifted by 5 in order to match the text position 5 with a parameter having a value of zero. By referring to table T3, it is seen that the text pointer must be shifted by 4. Since table T2 produces a larger shift amount the text pointer is shifted by 5 positions so that the aligned portion of text string T is now as shown:

T: aZaBaaC

The aligned encoded portions of pattern string P and text string T are as follows:

| position | 1234567 |
|---|---|
| revprev(P): | 03aa2a0 |
| revprev(T): | a0a0aa0 |

In this instance a mismatch occurs at revprev(P) position 5. Since the mismatch is between a parameter (in revprev(P)) and a non-zero constant a (in revprev(T)), tables T1 and T3 are referred to to determine the amount in which the text pointer must be shifted. The value corresponding to constant a in table T1 is equal to 1 (T1[a]=1). The value corresponding to position 5 in table T3 is equal to 4(T3[5]

=4). Since the shifted value in table T3 is greater than T1, the text pointer is shifted by 4 so that the aligned portion of text string T is now as shown:

T: aBaaCbB

The aligned encoded portions of pattern string P and text string T are as shown:

| position | 1234567 |
|---|---|
| revprev(P): | 03aa2a0 |
| revprev(T): | a5aa0b0 |

In this instance, a mismatch occurs at revprev(P) position 6 and the mismatched character k is a b. Tables T1 and T3 are referred to to determine the amount in which the text pointer must be shifted. Since the constant b does not occur in revprev(P), table T1 is equal to 7 (T1[b]=7). Table T3 is equal to 2(T3[6]=2). Since the value from table T1 is higher, the text pointer is shifted by seven positions to pass the point of mismatch so that the original portion of text string T is now as shown:

T: BCaaCaC

The aligned encoded portions of pattern string P and text string T are as follows:

| position | 1234567 |
|---|---|
| revprev(P): | 03aa2a0 |
| revprev(T): | 03aa2a0 |

At this point a match between the revprev(P) and the revprev(P) has occurred. The text pointer is then shirred beyond the match which causes the revprev(P) to overreach revprev(P) as shown:

| position: | 1234567 |
|---|---|
| revprev(P): | 03aa2a0 |
| revprev(T): | 0a2aa0 |
| T: | CaBaaB |

At this point, the pattern matching is complete and one match has been found.

Other kinds of shifts may be performed to determine the shifting of the text pointer and ultimately the pattern string P besides those described above. The shift performed using table T3 will hereinafter be referred to as the self aligning shift. In performing a self aligning shift, the longest matching substring of the pattern string and the text string is identified and stored in memory. After the self aligning shift has been performed, a substring of revprev(T) which matched a substring of revprev(P) in a previous stage now matches the shifted portion of revprev(P) in a current stage. This information can be used to perform a new type of shift operation which may result in shifting the pattern by a larger number of positions than the self aligning shift.

In accordance with one aspect of the present invention, following a self aligning shift, a "turbo" shift or a "jump" operation can be performed. Turbo shift and jump operations for regular strings have been described in M. Crochemore et al., "Speeding up two string-matching algorithms," in 9th Annual Symposium on Theoretical Aspects of Computer Science (STACS 92), Lecture Notes in Computer Science 577, Cachan, France, February 1992, pp. 589–600. The turbo shift is used when the length of a current matching substring is less than the length of a previous matching substring. The turbo shift shifts the pattern string P by the difference in length between the previous matching substring and current matching substring. If the shift resulting from a self aligning shift was of distance d, the self aligning shift definitions guarantee that the previous matching substring matches another substring d positions to the left in pattern string P.

However, as illustrated in FIG. 4, when encoded strings are being compared, i.e., those strings subjected to the revprev function, the number of shifted positions will depend upon the comparison of substrings as opposed to the comparison of single characters. This is because the encoded characters do not have a well-defined set of equalities and further can be redefined within the text as the pattern string is shifted.

Figure 14:
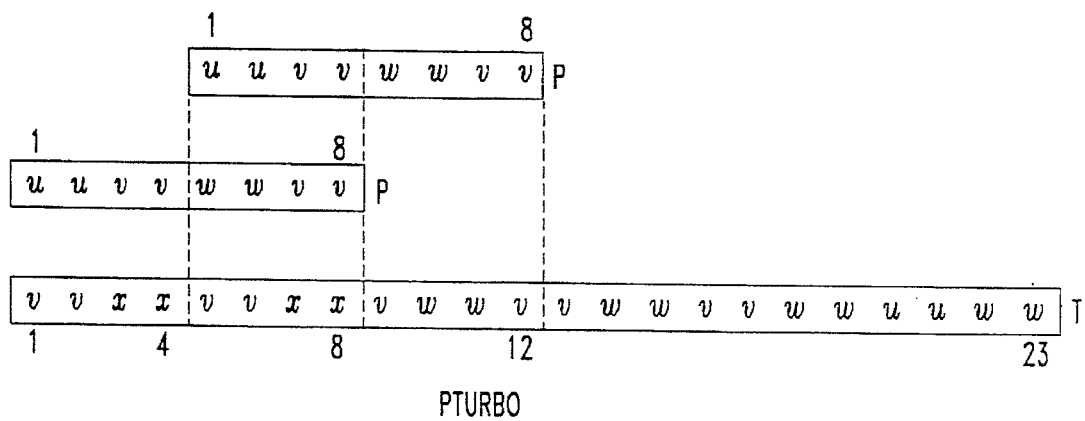
FIG. 14 illustrates a turbo shift operation in accordance with the present invention.

For example, let P=uuvvwwvv and T= vvxxvvxxvwwv-vwwvvwwuuww, where u,v,w and x are parameters. As illustrated in FIG. 14 if P[1] (where P[1] represents the first position of pattern string P) is aligned with T[1], a mismatch is found in the right to left direction to occur at position 2. If the self aligning shift is used, the text pointer is shifted by four positions so that P[1] is aligned with T[5]. Thus, uuvv of pattern string P is aligned with the previous position of wwvv. The portion of text string T currently aligned with pattern string P is now vvxxvwwv. When scanning in a right to left direction, the first mismatch occurs at the next to rightmost symbol v of pattern string P, which corresponds to symbol w in text string T. The symbol four symbols to the left of mismatched symbol w in text string T is a symbol x. Since the length of the previous matching substring is four and the length of the current matching substring is one, the turbo shift shifts the pattern by difference, which is three positions. By using a turbo shift operation as opposed to a self aligning shift, the pattern is shifted by three positions rather than one position.

A second type of operation which may be performed after a self aligning shift operation is a jump operation. The purpose of a jump operation is to avoid looking at every symbol in a current stage when the symbols have already been looked at in a previous stage. A jump operation may be performed to "jump" over substrings of text string T and pattern string P that are known to match from a previous self aligning shift operation. For regular strings, if it is determined that a substring S of pattern string P matches a substring V of text string T and the text pointer is located at the right end of substring R of pattern string P and substring U of text string T that are known to match from a previous self aligning shift operation, the text pointer can jump directly to the left of substrings R and U knowing that RS=UV. However in parameterized strings, it would be possible for R to match U and S to match V and RS not to match UV because of inconsistencies in the parameter pairings. For example, an x occurring in R may be paired with a Y occurring in U, while an x occurring in S may be paired with a Z occurring in V. As such, a determination must be made as to whether a "full" jump or a "partial" jump can be performed.

Figure 15:
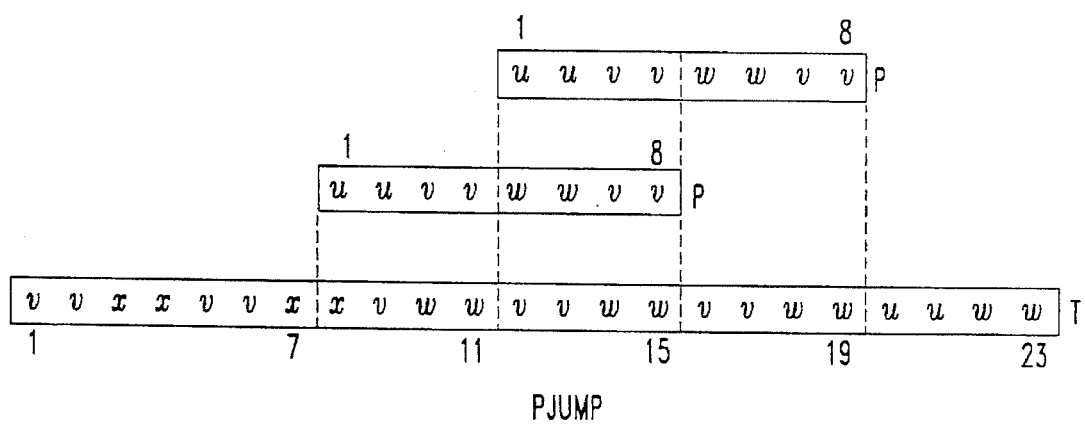
FIG. 15 illustrates a jump operation in accordance with the present invention.

Continuing with the above example as illustrated in FIG. 15, where P[1] is now aligned with T[8], the portion of the text string T aligned with P is xvwwvvww. The first mismatch identified in a right to left direction is at P[2]. A self aligning shift operation causes the pattern to be shifted by four positions so that P[1] is aligned with T[12] and P[1,4] is known to match T[12,15]. By scanning in a right to left direction it is further determined that p[5,8]=T[16,19]. As can be seen, pattern string P does not match text substring T[12,19]=vvwwvvww. The rightmost position at which the substring fails to match encoded pattern string P is at P[2]=u and which is located in the middle of P[1,4]=uuvv.

A data structure is used to keep track of the pairing of the encoded parameters determined by the previous stage and the current stage so that a determination is made that P[3,8]=T[14,19] and that a mismatch occurs at P[2] without having to scan all of P[1,4]. The data structure keeps track of the rightmost position in the text at which each parameter pairing occurs. This rightmost position is used to determine if the parameter pairing is current. In each stage, the information from the previous stage is saved in one such data structure. When performing the right to left comparison, a new data structure is created which stores the new information. When a substring is reached which matches part of the text in a previous stage, the information from the new stage is inserted into the data structure representing the previous stage. While inserting the information, conflicts between the pairings are identified. If conflicts are found, the rightmost conflict is monitored from the previous matching stage :which indicates the length of the partial jump. If no conflicts are found, a full jump is performed. The data structure can be implemented using any known method such as, but not limited to, using lists, balanced trees or hashing.

LINEAR STRINGS FOR SQUARE MATRICES (LSTRINGS)

Figure 8:
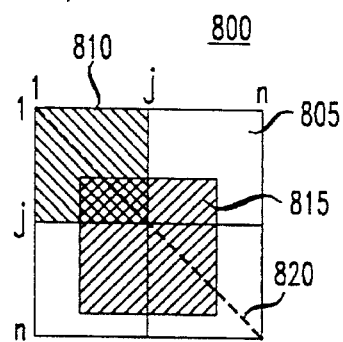
FIG. 8 illustrates a n×n matrix A in accordance with the present invention.

Referring to FIG. 8, there is shown a n×n matrix 800 which is denoted by A[1:n, 1:n]. A jth suffix 805 of matrix A is defined for $1 \leq j \leq n$, as A[j:n, j:n] and a jth prefix 810 of matrix A is defined as A[1:j, 1:j]. Any square submatrix S 815 whose upper left corner lies on the main diagonal 820 of A is defined to be a prefix of a suffix of A. Each diagonal of A is numbered by d if its elements are A[i,j] with i−j=d and $0 \leq d \leq n-1$.

Figure 9A:
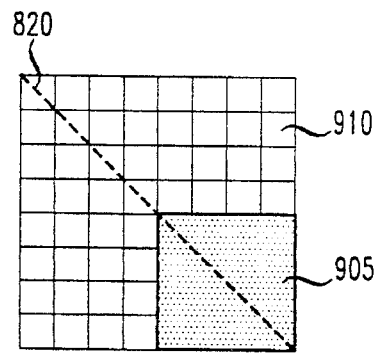
FIG. 9a–9d illustrate various prefixes and suffixes of the matrix A of FIG. 6.
Figure 9B:
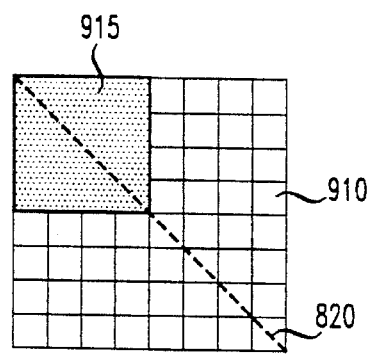
Figure 9C:
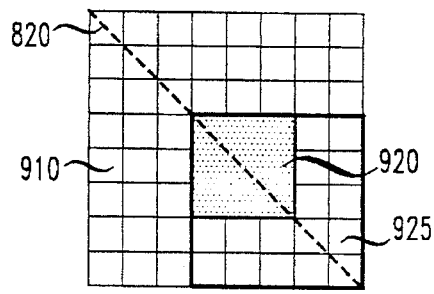

FIGS. 9a–9d illustrate various prefixes and suffixes of matrix A. FIG. 9a illustrates a 5th suffix 905 of A. In general, an ith suffix of A is identified by the subsquare 910 of the main diagonal 820 at which the suffix begins. FIG. 9b illustrates a 4th prefix 915 of matrix A. In general, an ith prefix of a matrix is determined by figuring out how many subsquares 910 of the main diagonal 820 are occupied by the prefix. Combining these two principles FIG. 9c illustrates a 3rd prefix 920 of a 4th suffix 925 of matrix A. As can be seen, the suffix 925 begins at the fourth subsquare 910 of the diagonal 820 and the prefix 920 encompasses the first three subsquares 910 of the main diagonal 820 contained within the suffix 925.

Figure 9D:
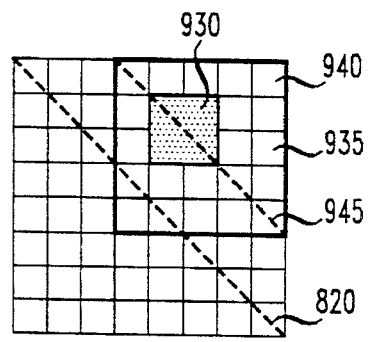

Likewise, prefixes and suffixes of submatrices not located on the main diagonal can also be represented in this manner. FIG. 9d illustrates the second prefix 930 of the second suffix 935 of submatrix $A_{-3}$ 940. The notation $A_{-3}$ indicates that the left upper corner of the submatrix is located at the third main diagonal relative to the main diagonal 820. The prefix and suffix notation of the submatrix is analogous to that of the main matrix A but refers to the positional relationship with respect to the main diagonal $d_{-3}$ 945 within the submatrix.

Figure 10A:
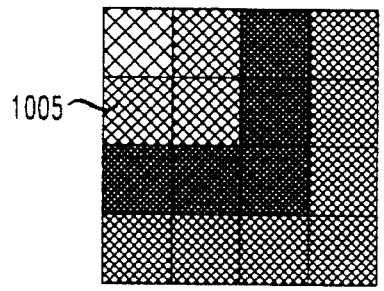

Referring to FIGS. 10a–10d, the matrix A can be converted to a linear representation which is referred m as a linear string (Lstring). Referring to FIG. 10a, the matrix A[1:n, 1:n] is divided into n L-shaped characters 1005 from an alphabet of L-shaped characters, L$\Sigma$, the ith L-shaped ,character comprising row A[i,1:i−] and column A[1:i,i]. Referring to FIG. 10b, the L-shaped characters 1005 can further be represented in one dimension in an L string 1010 by arranging the L-shaped characters 1005 in an order determined by their top-down appearance in A. Two L-shaped characters are equal if the Lcharacters 1005 are equal as strings over the alphabet $\Sigma$. Two Lcharacters can be concatenated by concatenating the strings corresponding to each Lcharacter. Referring to FIG. 10c, a series of Lcharacters 1005 which are concatenated are referred to as chunks 1015 which are obtained by labeling the L-shaped characters 1005 of A in one dimension in the order given by their top-down appearance in A, starting at row k and ending at row j. While an Lstring 1010 represents an entire matrix, a chunk 1015 represents a given portion of a matrix. However, an Lstring 1010 can also be used to represent a chunk 1015 as illustrated in FIG. 10d. FIG. 10d illustrates an Lstring 1020 for the chunk 1015 illustrated in FIG. 10c.

LINEAR SUFFIX TREES (L-SUFFIX TREES)

An L-suffix tree is constructed so ;that given a square matrix A[1:n, 1:n], a path is provided within the tree which corresponds to each square submatrix of A. Each square submatrix of A is established by determining the suffixes of matrix A. Square submatrices of A having common prefixes share the same path on the tree. In addition, each submatrix of A must be a prefix to some suffix of A so that a correspondence can be realized between all submatrices of A and the paths of the tree by considering only the suffixes of A.

Each matrix which is to be represented in the tree is transformed to a linear representation of Lcharacters as discussed above. The Lcharacters are further broken down to a set of Lsuffixes which represent the matrix. Preferably the bottom row and rightmost column of the matrix is augmented with the symbol $ so that each row and column of the matrix end with a unique endmarker.

Referring to FIG. 11a, there is shown a matrix 1100 which includes a bottom row 1105 and rightmost column 1110 which contains a unique endmarker. The numbers on top of the first row and adjacent the first column represent the positional relationship of each square within the matrix. FIG. 11b illustrates an Lstring 1115 for the matrix 1100 illustrated in FIG. 11a. Above each symbol 1120 in the Lstring 1115 is the positional notation corresponding to the symbol's position within the matrix 1100.

An Lsuffix tree $LT_a$ is constructed by inserting each Lsuffix of a matrix A from the longest suffix to the shortest suffix into a tree of initially one node referred to as the root. As each Lsuffix is added to the tree, internal nodes are created based on common Lprefixes between two or more of the Lsuffixes. Each internal node within the tree must have at least two offspring. Edges connecting the nodes are labeled by Lcharacters or chunks. Chunks or Lcharacters which are assigned to offspring edges start with different Lcharacters which are of the same length as strings in $\Sigma^*$. The concatenation of the chunks labeling the edges on a path from the root to a leaf provides one Lsuffix of the matrix. As such, there is a one to one correspondence between the leaves of the tree $LT_a$ and the Lsuffixes of the matrix A.

Figure 12:
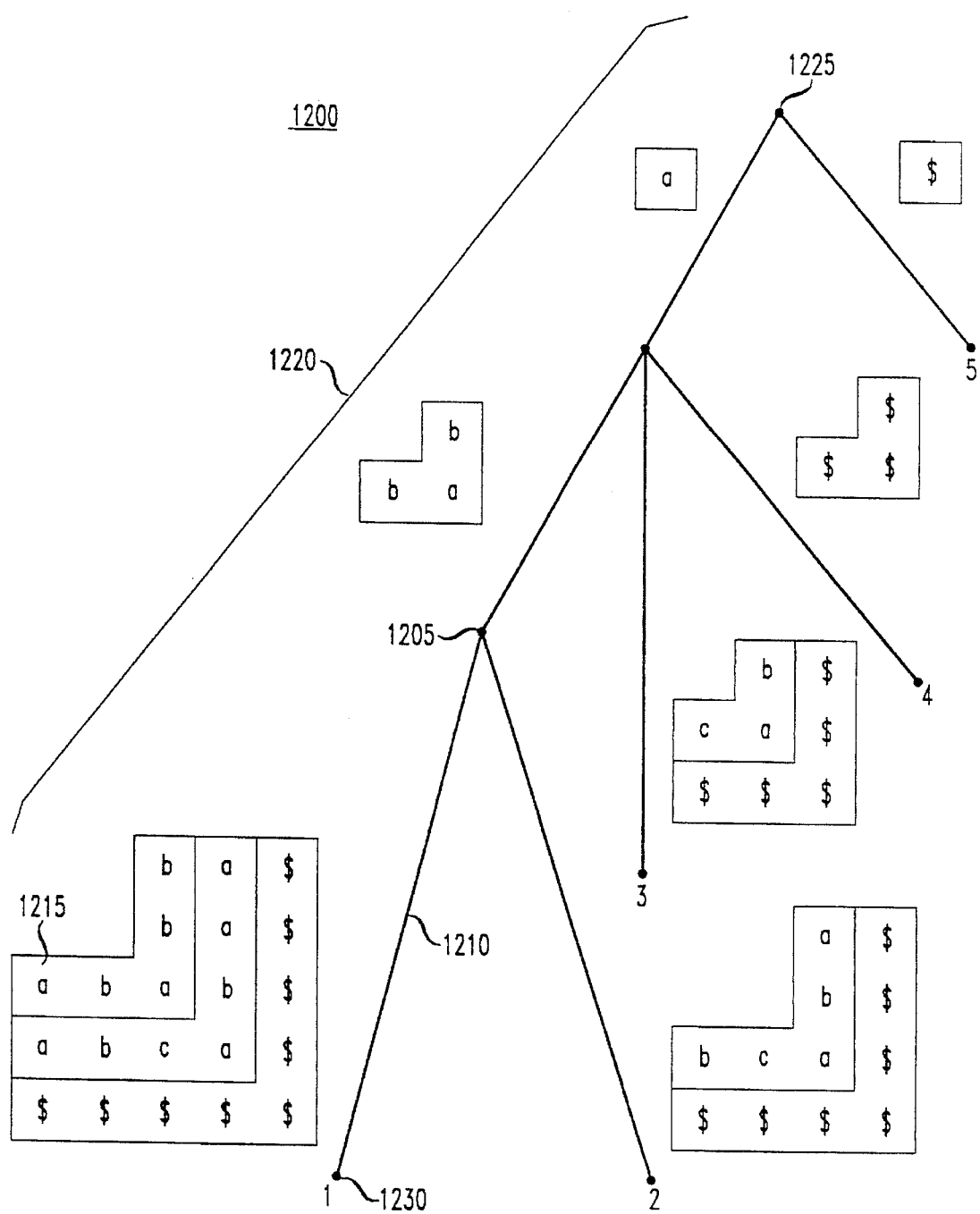

Referring to FIG. 12, there is shown an Lsuffix tree 1200 for the matrix in FIG. 12a. Each internal node 1205 within the tree 1200 contains at least two offspring 1210 which are labeled by chunks 1215. Each Lsuffix 1220 is represented by the concatenation of labels from a root 1225 of the tree 1200 to each leaf 1230.

A node u is defined to be a locus of an Lstring (Lα) within the Lsuffix tree LT if the concatenation of the labels on the path from the root of LT to u is equal to Lα. An extension of Lα is defined to be any Lstring of which Lα is an Lprefix. An extended locus of Lα is defined to be a locus of the shortest extension of Lα whose locus is defined in LT. A contracted locus of Lσ is defined to be a locus of the longest Lprefix of Lα whose locus is defined in LT.

CONSTRUCTING AN LSUFFIX TREE

An Lsuffix tree $LT_i$ is a compacted trie over the alphabet $L\Sigma$ that represents the suffixes $A[j:n+1, j:n+1]$ for $1 \leq j \leq i$ of matrix A as Lstrings. For each stage i an L suffix is added to the tree $LT_{i-1}$ thereby producing tree $LT_i$. An Lstring corresponding to a longest prefix of $A[i:n+1, i:n+1]$ that is also a prefix of $A[j:n+1, j:n+1]$ is referred to as $Lhead_i$. Because $Lhead_i$ occurs at least once in the Lsuffix tree LT, it must have a locus defined in $LT_i$. However, $Lhead_i$ may not have a locus defined in the Lsuffix tree $LT_{i-1}$. Each L string which is inserted in the tree $LT_{i-1}$, shares a path with an existing path within the tree i.e., a common L prefix with another L suffix, until there is an uncommon symbol. At that point, a node is inserted and a new leaf is attached to the node which is labeled by the L suffix thereby producing tree $LT_i$.

As discussed above, square matrices do not follow the Distinct Right Context property for strings. As such, suffix kinks cannot be defined in the Lsuffix tree in the ordinary manner. In order to define suffix links for an Lsuffix tree the locus of $Lhead_{i-1}$ is defined as $v \in LT_{i-1}$ and the locus of $Lsuffix_{i-1}$ is defined as $g \in LT_{i-1}$. Suffix links for all of the leaves of $LT_{i-1}$ with the exception of g can now be defined. For each leaf $q \in LT_{i-1}$ and q not equal to g, the locus of the Lstring corresponding to $A[j:n+1, j:n+1]$, i.e., Lsuffix j for $j \leq i-1$, there is a suffix link pointing to leaf w, where w is the locus of the Lstring corresponding to $A[j+1:n+1, j+1:n+1]$, i.e., $Lsuffix_{j+1}$. The suffix link for leaf q is denoted by $SL(q)=w$.

When $Lhead_i$ has a locus defined in $LT_{i-1}$, it is identified so that a leaf offspring can be created for that locus. If $Lhead_i$ does not have a locus defined in $LT_{i-1}$, the node is created as an offspring of the contracted locus of $Lhead_i$ in the tree. The Lstring, Lα is defined as corresponding to $A[i:i+h-1, i:i+h-1]$, where $h=\min(0, 1_{i-1, -1})$. Lα is the Lprefix of $Lhead_i$ and has an extended locus r' in $LT_{i-1}$. The extended locus r' is an ancestor of any leaf $u=SL(q)$, where q is not equal to g is any leaf descendant of v. The contracted locus u of Lα in $LT_{i-1}$ is the parent of r', when Lα does not have a locus defined in $LT_{i-1}$.

To find the contracted locus of u of Lα, a rescanning procedure is used in which the node u is first identified from which the search is initiated. In order to find the contracted locus u of Lα in the tree $LT_{i-1}$ the procedure findlocus is followed. It is assumed that the v is not equal to $root(LT_{i-1})$, i.e., the locus of $Lhead_{i-1}$ in $LT_{i-1}$. The findlocus procedure begins by selecting any offspring c of v which is not equal to the leaf g. The leaf q of the tree $LT_{i-1}$ is pointed to by c. On the path from the root of $LT_{i-1}$ to SL(q), u is the deepest node such that $1(u) \leq h$, where l(u) is the length of the Lstring where u is the locus and $h=\min(0, 1_{i-1}, -1)$.

Once node u is identified, the contracted locus of $Lhead_i$ can be located by using a scanning procedure referred to as findpath. If the contracted locus u of Lα is root $(LT_{i,j})$, the findlocus procedure is skipped and the findpath procedure is initiated to find the contracted focus of Lhead i. In findpath, the only offspring r of node u is selected so that the first Lcharacter of the chunk on the edge (u,r) is $A[i+1(u), 1:i+1(u)-1]A[1:i+1(u), i+1(u)]$, i.e., the Lcharacter equal to $Lsuffix[1(u)+1]$. If no such offspring exists, the locus of $Lhead_i$ is equal to the extended locus of $Lhead_i$ in $LT_{i-1}$. If the offspring r exists, the extended locus of $Lhead_i$ in $1LT_i-1$ (f) must be located. The findpath procedure skips the first $h-1(u)$ Lcharacters of the chunk on the edge (u,r), i.e., they are not compared against the corresponding Lcharacters of the Lstring obtained from $A[i:n+1, i:n+1]$. This essentially results in the skipping of the matrix corresponding to Lalpha. The findpath procedure compares one by one and from left to right, the remaining (skipping Lα) Lcharacters of $A[i:n+1, i:n+1]$ with the corresponding ones on the edge of the path from u to f. The findpath procedure continues the comparison until a difference in characters is detected. That identifier is the contracted locus of $Lhead_i$.

Once the contracted locus of $Lhead_i$ or the locus $Lhead_i$ is located, an updatetree procedure is initiated which transforms the tree $LT_{i-1}$ into $LT_i$. If the locus of $Lhead_i$ in $LT_{i-1}(w)$ is identified, a leaf g' is created as an offspring of the locus. The edge (w,g') is labeled with a triple $(1(w)+1, n+1, i)$ that corresponds to the chunk obtained by deleting $Lhead_i$ from the $Lsuffix_i$.

If w is the contracted locus of $Lhead_i$ in $LT_{i-1}$, a new node w' is created as the locus of $Lhead_1$ by splitting an edge (w,f), i.e., w' is made an offspring of w. The edge (w,f) is labeled by $(p_1, p_2, j)$. The label on the edge (w, w') is set to $(p_1, p_1+1_i-1(w)-1, j)$ and the one on the edge (w',f) to $(p_1+1_i-1(w)-1, p_2, j)$. The concatenation of the Lstring of which w is the locus with the first $1_i-1$ (w) Lcharacters of the chunk of the edge (w,f) is equal to $Lhead_i$. Furthermore, the concatenation of the chunks on the edges (w,w') and (w',f) gives the chunk on the former edge (w,f).

STATISTICAL ANALYSIS USING LSUFFIX TREES

An Lsuffix tree can be used to answer statistical queries about the structure of a TEXT matrix. An Lsuffix tree is constructed for the TEXT matrix as described above. From the TEXT realfix, queries can be answered such as determining the largest square matrix that appears in position A[i,j] of TEXT, or if given two pattern square matrices of TEXT, determining the longest prefix the pattern matrices have in common. The Lsuffix tree can also be used to determine the number of occurrences a particular submatrix of TEXT occurs in the TEXT matrix. The procedures for answering these statistical queries are the same procedures used to construct the Lsuffix tree, i.e., the findlocus and findpath procedures.

The procedure used to find $Lh_{i,d}$ is similar to that for finding $Lhead_i$. The procedure first looks for input v which is the extended locus of $Lh_{i-1,d}$. If $v=root(LT)$ then locus $u=root(LT)$ and the rescanning procedure findlocus as discussed above is skipped. If v is not equal to root(LT), the rescanning procedure is used to locate the contracted locus u of Lγ. Once the contracted locus u is identified, a scanning procedure is performed which starts at u and skips Lγ to find the extended locus of $Lh_{i,d}$.

REFINING THE LSUFFIX TREE

In some cases, the Lsuffix tree may need to be refined so that more intricate searching can be accomplished. As such, a refined Lsuffix tree $RLT_D$ as shown in FIG. 12 can be constructed which represents the same information as in the Lsuffix tree $LT_D$ but in a different format. For a given internal node $v \in LT_D$, the number of offsprings of v is represented by off(v) which are then sorted by the first Lcharacter of the chunks on the corresponding edges and listed by the notation $w_1 < \ldots < w_{off(v)}$. A string which corresponds to the chunk on the edge $(v, w_i)$ where $1 < i < off(v)$ is referred to as $\beta_i$. For each internal node $v \in LT_D$ a contracted trie PT(v) is built which is defined over Σ which represents as strings in Σ, the chunks on the edges outgoing from v, i.e., $\beta_i \ldots \beta_{off(v)}$. Therefore, each edge of PT(v) has a string assigned to it which is a substring of some $\beta_i$. The root of PT(v) corresponds to v. The tries are attached based on the parent-offspring relation in $LT_D$, i.e., for each edge (v, f) $\in LT_D$, the root of PT(f) is Coalesced with the leaf corresponding to it in PT(v) which results in the tree $RLT_D$.

PATTERN RETRIEVAL USING THE REFINED LSUFFIX TREE

Pattern retrieval can be used to preprocess a TEXT matrix to build an index data structure that represents all substrings of the text. In addition, the data structure can be used to report all occurrences of a pattern matrix PAT in the TEXT matrix. Pattern retrieval can also be used for statistical queries regarding the structure of the text, e.g., finding the longest repeated substring of the text.

Prior to beginning the pattern retrieval procedure, an Lsuffix tree LTD is constructed for the TEXT matrix and refined in the manner described above. An Lstring Lpat is created to represent the matrix PAT. Lpat occurs in the matrix TEXT if Lpat has an extended locus in tree RLTD. The pattern retrieval procedure essentially identifies the set of suffixes within the TEXT matrix that include the PAT matrix as a prefix.

The foregoing merely illustrates the principles of the invention and it will thus be appreciated that those skilled in the art will be able to devise numerous alternative arrangements which, although not explicitly described herein, embody the principles of the invention and are within the scope and spirit.

We claim:

1. A method of matching a pattern data string with a text data string, said pattern data string and text data string being comprised of parameter characters and constant characters, said pattern data string containing fewer numbers of characters than said text string, the method comprising the steps of:
   a) substituting the parameter characters within the pattern data string with a numerical character, each numerical character being chosen to point to a proximate instance of said parameter character in said pattern data string, said substitution occurring in a right to left direction;
   b) aligning the pattern data string with a portion of the text data string;
   c) substituting the parameter characters within at least the aligned portion of the text data string with a numerical character, each numerical character being chosen to point to a proximate instance of said parameter character in said text data string, said substitution occurring in a right to left direction;
   d) comparing said aligned portion of said pattern data string with said text data string in a right to left direction;
   e) identifying a first occurrence of a mismatch between the pattern data string and the text data string;
   f) identifying a match between said pattern string and said aligned portion of said text string if no mismatch occurs;
   g) determining the number of positions required to shift the pattern data string relative to the text data string so that the mismatched character in the text data string is aligned with a proximate occurrence of a like character in the pattern data string, said determination considering the relationship between characters adjacent to the mismatched character; and
   h) repeating steps b)–g) and identifying every occurrence where a portion of the text string matches the pattern data string.

2. The method of claim 1 wherein said step of determining the number of positions required to shift the pattern data string comprises the step of determining the maximum number of positions in which the pattern data string can be shifted relative to the text string provided that no matches are passed over and that the shift pattern string results in a favorable possibility of a match between the pattern string and the text string.

3. The method of claim 2 wherein said step of determining the number of positions to shift the pattern string further comprises the steps of:
   precomputing tables prior to the comparison of the pattern string to the text string which determine the number of positions to shift the pattern string relative to the text string based only on the characteristics of the pattern string and the relative position of each character within the pattern string relative to other like characters in the pattern string.

4. A method of matching at least a portion of a pattern data string with a text data string, said pattern data string and text data string being comprised of parameter characters and constant characters, the method comprising the steps of:
   a) substituting the parameter characters within the pattern data string with a numerical character, each numerical character being chosen to point to a proximate instance of said parameter character in said pattern data string, said substitution occurring in a right to left direction;
   b) creating at least one table, said table being based on known pattern string information and which represents relationships between symbols in said substituted pattern string, said relationships establishing a lower bound which determines the number of consecutive positions to shift a pointer with respect to the text string;
   c) aligning the pattern data string with a portion of the text data string;
   d) substituting the parameter characters within at least the aligned portion of the text data string with a numerical character, each numerical character being chosen to point to a proximate instance of said parameter character in said text data string, said substitution occurring in a right to left direction;
   e) comparing said aligned portion of said pattern data string with said text data string in a right to left direction;
   f) identifying a first occurrence of a mismatch between the pattern data string and the text data string;
   g) identifying a match between said pattern string and said aligned portion of said text string if no mismatch occurs;
   h) determining the number of positions to shift the pointer based on information obtained from the at least one table, said information being a function of the mismatched character identified in the text string, said determination considering the relationship between characters adjacent to the mismatched character; and
   i) repeating steps b)–h) and identifying every occurrence where a portion of the text string matches the pattern data string.

5. The method according to claim 4 wherein each parameter character contained in the pattern string represents a place holder for an actual character contained in the text string, each place holder of a particular parameter designation being bound by said actual character in said aligned portion of said text string once a pairing between said particular parameter designation and said actual parameter occurs.

6. The method according to claim 5 wherein said binding of said actual parameter to said particular parameter designation occurs for each aligned portion of the text string.

* * * * *